US00PP31612P2

(12) United States Plant Patent
Misato et al.

(10) Patent No.: US PP31,612 P2
(45) Date of Patent: Mar. 31, 2020

(54) ***MANDEVILLA* PLANT NAMED 'SUNPA 5223'**

(50) Latin Name: *Mandevilla hybrida*
Varietal Denomination: Sunpa 5223

(71) Applicants: Tomoya Misato, Shiga (JP); Masahiro Yamada, Shiga (JP)

(72) Inventors: Tomoya Misato, Shiga (JP); Masahiro Yamada, Shiga (JP)

(73) Assignee: Suntory Flowers, Limited, Tokyo (JP)

( * ) Notice: Subject to any disclaimer, the term of this patent is extended or adjusted under 35 U.S.C. 154(b) by 0 days.

(21) Appl. No.: 16/350,643

(22) Filed: Dec. 14, 2018

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'Sunpa 5223', characterized by its climbing plant habit; vigorous growth habit; freely branching habit; early and freely flowering habit; long flowering period; and small bright red-colored flowers.

1 Drawing Sheet

Botanical designation: *Mandevilla hybrida.*
Cultivar denomination: 'SUNPA 5223'.

BACKGROUND OF THE INVENTION

The present invention relates to a new and distinct cultivar of *Mandevilla* plant, botanically known as *Mandevilla hybrida* and hereinafter referred to by the name 'Sunpa 5223'.

The new *Mandevilla* plant is a product of a planned breeding program conducted by the Inventors in Higashiomi, Shiga, Japan. The objective of the breeding program is to create new freely branching *Mandevilla* plants with freely flowering habit and attractive flowers.

The new *Mandevilla* plant originated from a cross-pollination in Higashiomi, Shiga, Japan in May, 2014 of a proprietary selection of *Mandevilla hybrida* identified as code number 07M-9-1, not patented, as the female, or seed parent with a proprietary selection of *Mandevilla hybrida* identified as code number MH43, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in September, 2015.

Asexual reproduction of the new *Mandevilla* plant by terminal vegetative cuttings in Higashiomi, Shiga, Japan since March, 2016 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 5223'. These characteristics in combination distinguish 'Sunpa 5223' as a new and distinct *Mandevilla* plant:

1. Climbing plant habit.
2. Vigorous growth habit.
3. Freely branching habit.
4. Early and freely flowering habit.
5. Long flowering period.
6. Relatively small bright red-colored flowers.

Plants of the new *Mandevilla* can be compared to plants of the female parent selection. Plants of the new *Mandevilla* differ primarily from plants of the female parent selection in flower color as plants of the new *Mandevilla* have bright red-colored flowers whereas plants of the female parent selection have pink-colored flowers.

Plants of the new *Mandevilla* can be compared to plants of the male parent selection. Plants of the new *Mandevilla* differ primarily from plants of the male parent selection in plant habit as plants of the new *Mandevilla* have a climbing plant habit whereas plants of the male parent selection have a semi-climbing plant habit.

Plants of the new *Mandevilla* can be compared to plants of the *Mandevilla amabilis* X *Mandevilla boliviensis* 'Sunmandecrim', disclosed in U.S. Plant Pat. No. 15,539. In side-by-side comparisons, plants of the new *Mandevilla* differ from plants of 'Sunmandecrim' in the following characteristics:

1. Plants of the new *Mandevilla* have a climbing plant habit whereas plants of 'Sunmandecrim' have a semi-climbing habit.
2. Plants of the new *Mandevilla* have shorter internodes than plants of 'Sunmandecrim'.
3. Plants of the new *Mandevilla* have darker green-colored leaves than plants of 'Sunmandecrim'.
4. Plants of the new *Mandevilla* have smaller flowers than plants of 'Sunmandecrim'.

5. Flowers of plants of the new *Mandevilla* do not fade with development whereas flowers of plants of 'Sunmandecrim' fade with development.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpa 5223' grown in a container.

The photograph at the bottom of the sheet is a close-up view of a typical flower and flower buds of 'Sunpa 5223'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunpa 5223'.

Parentage:

*Female, or seed, parent*.—Proprietary selection of *Mandevilla hybrida* identified as code number 07M-9-1, not patented.

*Male, or pollen, parent*.—Proprietary selection of *Mandevilla hybrida* identified as code number MH43, not patented.

Propagation:

*Type*.—By terminal vegetative cuttings.

*Time to initiate roots, summer and winter*.—About two weeks at temperatures about 23° C. to 25° C.

*Time to produce a rooted young plant, summer and winter*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Climbing plant habit; vigorous growth habit; freely branching habit.

*Plant height*.—About 114 cm.

*Lateral branch description*.—Length: About 78 cm. Diameter: About 4 mm. Internode length: About 4.1 cm. Strength: Strong, flexible. Texture: Smooth, glabrous. Color, developing: Close to 151A slightly tinged with close to N167A. Color, fully developed: Close to 177B.

Leaf description:

*Arrangement*.—Opposite, simple.

*Length*.—About 6 cm.

*Width*.—About 4.2 cm.

*Shape*.—Obovate.

*Apex*.—Acuminate.

*Base*.—Obtuse.

*Margin*.—Entire.

*Texture and luster, upper and lower surfaces*.—Slightly pubescent; slightly glossy.

*Venation pattern*.—Pinnate, reticulate.

*Color*.—Developing leaves, upper surface: Close to 144A. Developing leaves, lower surface: Close to 146C. Fully expanded leaves, upper surface: Close to between 137B and 146A; venation, close to 144B. Fully expanded leaves, lower surface: Close to 147C; venation, close to 145C.

*Petioles*.—Length: About 1 cm. Diameter: About 1.8 mm. Texture, upper and lower surfaces: Slightly pubescent. Color, upper and lower surfaces: Close to 144C.

Flower description:

*Flower type and habit*.—Single salverform flowers arranged in axillary racemes; flowers face upright to outwardly; freely flowering habit with about three to five flowers per inflorescence and about 48 flowers developing per plant.

*Natural flowering season*.—Early flowering habit, plants begin flowering about six weeks after planting; long flowering period, plants flower continuously from early summer until late autumn in Japan.

*Flower longevity on the plant*.—About seven to ten days; flowers not persistent.

*Fragrance*.—None detected.

*Flower buds*.—Height: About 5.5 cm. Diameter: About 9.1 mm. Shape: Obtrullate. Color: Distally, close to 53A; mid-section, close to 150C tinged with close to 50A; proximally, close to 8D.

*Flowers*.—Appearance: Salverform; flared trumpet, corolla fused and five-parted; flowers roughly star-shaped. Diameter: About 5 cm. Depth (length): About 5.4 cm. Throat diameter: About 1.4 cm. Tube length: About 1.7 cm. Tube diameter, proximally: About 2.7 mm.

*Corolla*.—Quantity and arrangement: Five petals arranged in a single whorl and fused towards the base into an elongated tube; petal lobes imbricate. Petal lobe length: About 2.2 cm. Petal lobe width: About 1.9 cm. Petal lobe shape: Obovate, asymmetrical. Petal lobe apex: Acute. Petal lobe margin: Entire; moderately undulate; slightly recurved. Petal lobe texture and luster, upper and lower surfaces: Smooth, glabrous; velvety; matte. Throat texture: Smooth, glabrous. Tube texture: Smooth, glabrous. Color: Petal lobe, when opening, upper surface: Close to 53A; at the margin, flushed with close to 187B. Petal lobe, when opening, lower surface: Close to 46A. Petal lobe, fully opened, upper surface: Close to N45A; venation, close to N45A; color does not fade with development. Petal lobe, fully opened, lower surface: Close to 46A; venation, close to 46A; color does not fade with development. Throat: Close to 53A and 34B; proximally, close to 28A; venation, close to N30B. Tube: Close to 53B; proximally, close to 4C; venation, close to 53B and 4C.

*Calyx*.—Quantity and arrangement: Five sepals arranged in a single whorl, fused at the base; calyx, star-shaped. Sepal length: About 7.8 mm. Sepal width: About 2.6 mm. Sepal shape: Lanceolate. Sepal apex: Acuminate. Sepal margin: Entire. Sepal texture, upper and lower surfaces: Pubescent. Sepal color, upper surface: Distally, close to N45C; proximally, close to 145C. Sepal color, lower surface: Distally, close to N45C; proximally, close to 145D.

*Peduncles*.—Length: About 2.2 cm. Diameter: About 2.2 mm. Texture: Pubescent. Aspect: Upright to outwardly. Color: Close to 144B.

*Pedicels*.—Length: About 1.6 cm. Diameter: About 1.7 mm. Texture: Pubescent. Aspect: Upright to outwardly. Color: Close to 144C.

*Reproductive organs*.—Stamens: Quantity and arrangement: Typically five; filaments fused to corolla; anthers, connivent. Anther size: About 1.6 mm by 8.7 mm. Anther shape: Lanceolate. Anther color: Close to 12B. Pollen amount: None observed. Pistils: Quantity: Typically one. Pistil length: About 1.8 cm. Style color: Close to 145D. Stigma shape: Globose. Stigma color: Close to 145B. Ovary color: Close to 145A.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 5223' as illustrated and described.

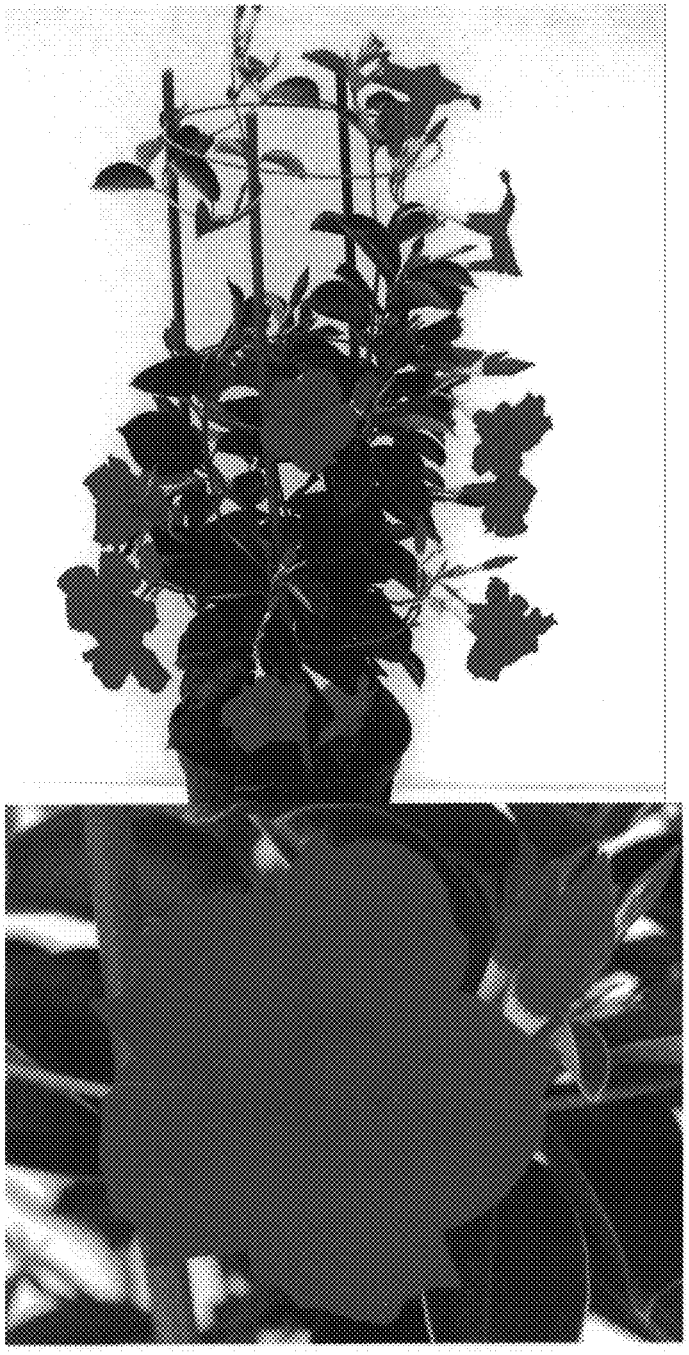

* * * * *